(12) United States Patent
Sato et al.

(10) Patent No.: US 9,735,279 B2
(45) Date of Patent: Aug. 15, 2017

(54) GAS SENSOR AND METHOD OF MANUFACTURING THE SAME

(71) Applicant: FUJITSU LIMITED, Kawasaki-shi, Kanagawa (JP)

(72) Inventors: Shintaro Sato, Atsugi (JP); Naoki Harada, Atsugi (JP); Hideyuki Jippo, Atsugi (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 15/054,528

(22) Filed: Feb. 26, 2016

(65) Prior Publication Data
US 2016/0290956 A1 Oct. 6, 2016

(30) Foreign Application Priority Data

Mar. 31, 2015 (JP) ................. 2015-073543

(51) Int. Cl.
*G01N 27/414* (2006.01)
*H01L 29/66* (2006.01)
*H01L 29/786* (2006.01)
*G01N 27/12* (2006.01)

(52) U.S. Cl.
CPC ..... *H01L 29/78684* (2013.01); *G01N 27/127* (2013.01)

(58) Field of Classification Search
CPC .......... G01N 27/4141; G01N 27/127; G01N 27/414; H01L 29/78684; H01L 29/66045
USPC .................... 257/253, 29; 438/495
See application file for complete search history.

(56) References Cited

U.S. PATENT DOCUMENTS

| 2014/0260545 | A1* | 9/2014 | Ruhl ................. G01N 27/14 73/31.05 |
| 2014/0260547 | A1* | 9/2014 | Balandin ........... G01N 27/414 73/31.06 |
| 2015/0280012 | A1* | 10/2015 | Sato ................. H01L 29/78684 257/29 |
| 2016/0126317 | A1* | 5/2016 | Kim .................. H01L 29/1606 257/29 |

FOREIGN PATENT DOCUMENTS

| JP | 09-2577396 | 10/1997 |
| JP | 3555739 | 8/2004 |
| JP | 2011-169634 | 9/2011 |

OTHER PUBLICATIONS

Jinming Cai et al., "Atomically precise bottom-up fabrication of graphene nanoribbons", Nature, vol. 466, pp. 470-473, Jul. 22, 2010 (4 pages).

* cited by examiner

*Primary Examiner* — Cuong Q Nguyen
*Assistant Examiner* — Tong-Ho Kim
(74) *Attorney, Agent, or Firm* — Fujitsu Patent Center

(57) ABSTRACT

A gas sensor includes: a channel layer in which a F-terminated GNR, a H-terminated GNR, and a F-terminated GNR whose edge portions are terminated with different modifying groups are bonded to each other; a source electrode formed on one end of the channel layer; and a drain electrode formed on the other end of the channel layer, in which a surface of the H-terminated GNR is exposed, and this exposed portion is a gas sensing part.

17 Claims, 18 Drawing Sheets

FIG. 4

| | Graphene H | F | Cl | OH | NH$_2$ | CH$_3$ |
|---|---|---|---|---|---|---|
| Conduction | 3 | 4.22 | 4.2 | 3.23 | 2.28 | 2.82 |
| Valence | 4.56 | 5.32 | 5.36 | 4.03 | 3.21 | 3.92 |
| Ef | 4.2 | 3.78 | 4.77 | 4.78 | 3.63 | 2.745 | 3.37 |
| Eg | | 1.56 | 1.1 | 1.16 | 0.8 | 0.93 | 1.1 |

H-TERMINATED GNR without NH$_3$

H-TERMINATED GNR with NH$_3$+H

| | WITHOUT NH$_3$ | cNH$_4$ |
|---|---|---|
| CONDUCTANCE (nS) @0.1V | 56.6 | 26,100 |

FIG. 19A npn

F–H–F (4.28 eV)
F–OH–F (4.2 eV)
Cl–CH$_3$–Cl (4.08 eV)
F–NH$_2$–F (3.76 eV)
H–CH$_3$–H (3.58 eV)
H–NH$_2$–H (3.26 eV)
OH–NH$_2$–OH (3.19eV)
CH$_3$–NH$_2$–CH$_3$ (3.06 eV)

FIG. 19B pnp

H–F–H
OH–F–OH
CH$_3$–Cl–CH$_3$
NH$_2$–F–NH$_2$
CH$_3$–H–CH$_3$
NH$_2$–OH–NH$_2$
NH$_2$–H–NH$_2$
NH$_2$–CH$_3$–NH$_2$

GAS SENSOR AND METHOD OF MANUFACTURING THE SAME

CROSS-REFERENCE TO RELATED APPLICATION

This application is based upon and claims the benefit of priority of the prior Japanese Patent Application No. 2015-073543, filed on Mar. 31, 2015, the entire contents of which are incorporated herein by reference.

FIELD

The embodiments discussed herein are directed to a gas sensor and a method of manufacturing the same.

BACKGROUND

In modern society, electronic devices represented by a computer, a smart phone and the like spread, the Internet is connected all over the world, and much information is exchanged. Up to now, such information has been mainly information created by human work in many cases. However, for more comfortable life, activities in which every data in real society is captured by sensors and utilized are carried out. In the near future, it is said that times of what is called "a trillion sensors" come, and it is desired that various data of environment, traffic, a condition of health, an appearance of exchange, and the like are collected to be utilized. For this purpose, a large number of various sensors become necessary, so that development of new sensors is actively progressing.

As one of the above sensors, there is a gas sensor. The gas sensor is desired not only to serve as environmental monitoring by detecting one such as, for example, a nitrogen oxide but also to enable utilization for monitoring the condition of health by detecting components of an expired gas, a skin gas, and the like produced from a human body.

[Patent Document 1] Japanese Patent No. 3555739
[Non-Patent Document 1] J. Cai et al., Nature 466 (2010) 470.

As gases necessary to be detected for health care, there are various ones such as, for example, ammonia, nonanal, methane, and acetone. In order to sense such various gases, there is a need to prepare a plurality of highly-sensitive gas sensors whose sensitivities are different for the respective gases. Under the present situation, a gas sensor utilizing an oxide semiconductor such as $SnO_2$ is used for sensing the ammonia and the like. However, the sensitivity of the above gas sensor is about dozens ppm, which is far less than the sensitivity necessary for sensing an organism gas (about ppb), and in addition, gas selectivity is also insufficient.

SUMMARY

An aspect of a gas sensor includes: a channel layer formed of a plurality of graphene bonded to each other, among which adjacent graphene have edge portions terminated with modifying groups different from each other; and a pair of electrodes formed on both ends of the channel layer, wherein in the channel layer, a part of a surface thereof is exposed, and the exposed portion is a gas sensing part.

An aspect of a method of manufacturing a gas sensor includes: forming a piece of graphene whose edge portion is terminated with one modifying group; forming at least part of the piece of graphene into another piece of graphene whose edge portion is terminated with another modifying group different from the one modifying group to form a channel layer in which the piece of graphene and the other piece of graphene are bonded to each other; and forming a pair of electrodes on both ends of the channel layer, wherein a part of a surface of the channel layer is exposed, and the exposed portion is a gas sensing part.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 4 is a view representing a table in which the energies at the bottoms of the conduction bands and the tops of the valence bands, Fermi levels, and energy gaps in the respective GNRs are summarized;

FIG. 19A and FIG. 19B are schematic views representing concrete examples of the npn structure and the pnp structure in channel layers with composite GNRs.

DESCRIPTION OF EMBODIMENTS

First, a basic technical structure of a gas sensor and a method of manufacturing the same according to embodiments will be described.

Figure 1:
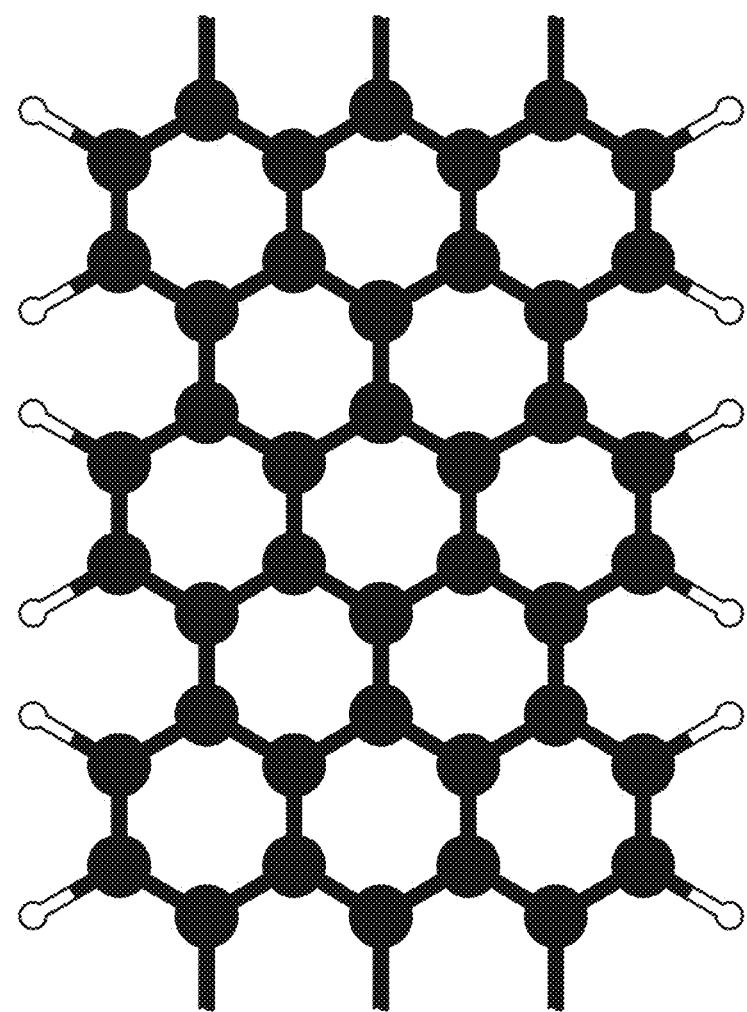
FIG. 1 is a view illustrating a H-terminated bottom-up graphene nanoribbon (GNR) formed from an anthracene dimer being a precursor.

In the embodiments, edges of graphene nanoribbons (GNR) are modified by various atoms, whereby GNRs different in work function and band gap are formed. In FIG. 1, a bottom-up GNR which is formed from an anthracene dimer being a precursor and whose edge portions are terminated with a modifying group, here, by hydrogen (H), is exemplified.

Figure 2:
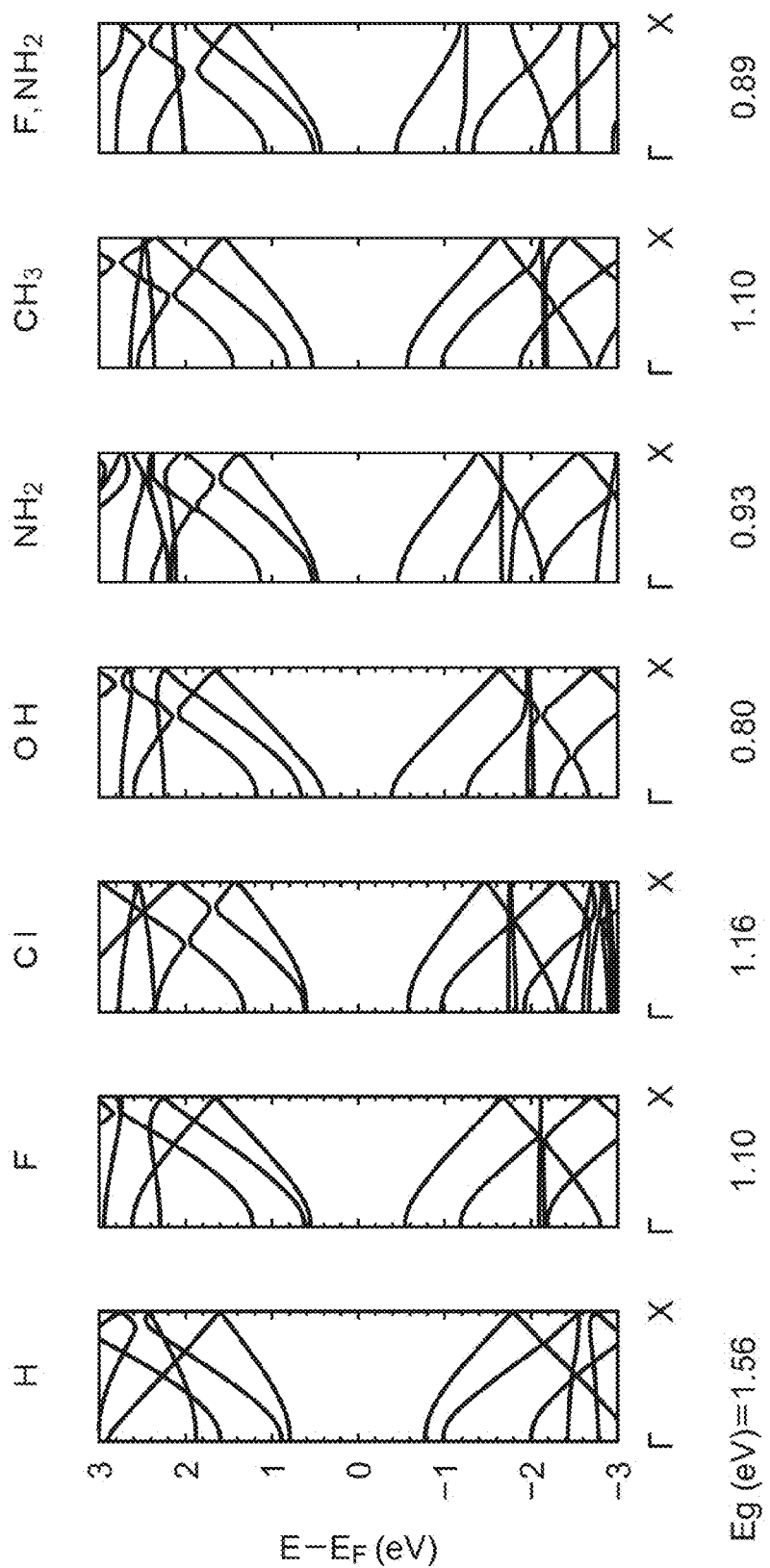
FIG. 2 is a view illustrating band structures of GNRs when modifying groups are variously changed.
Figure 3:
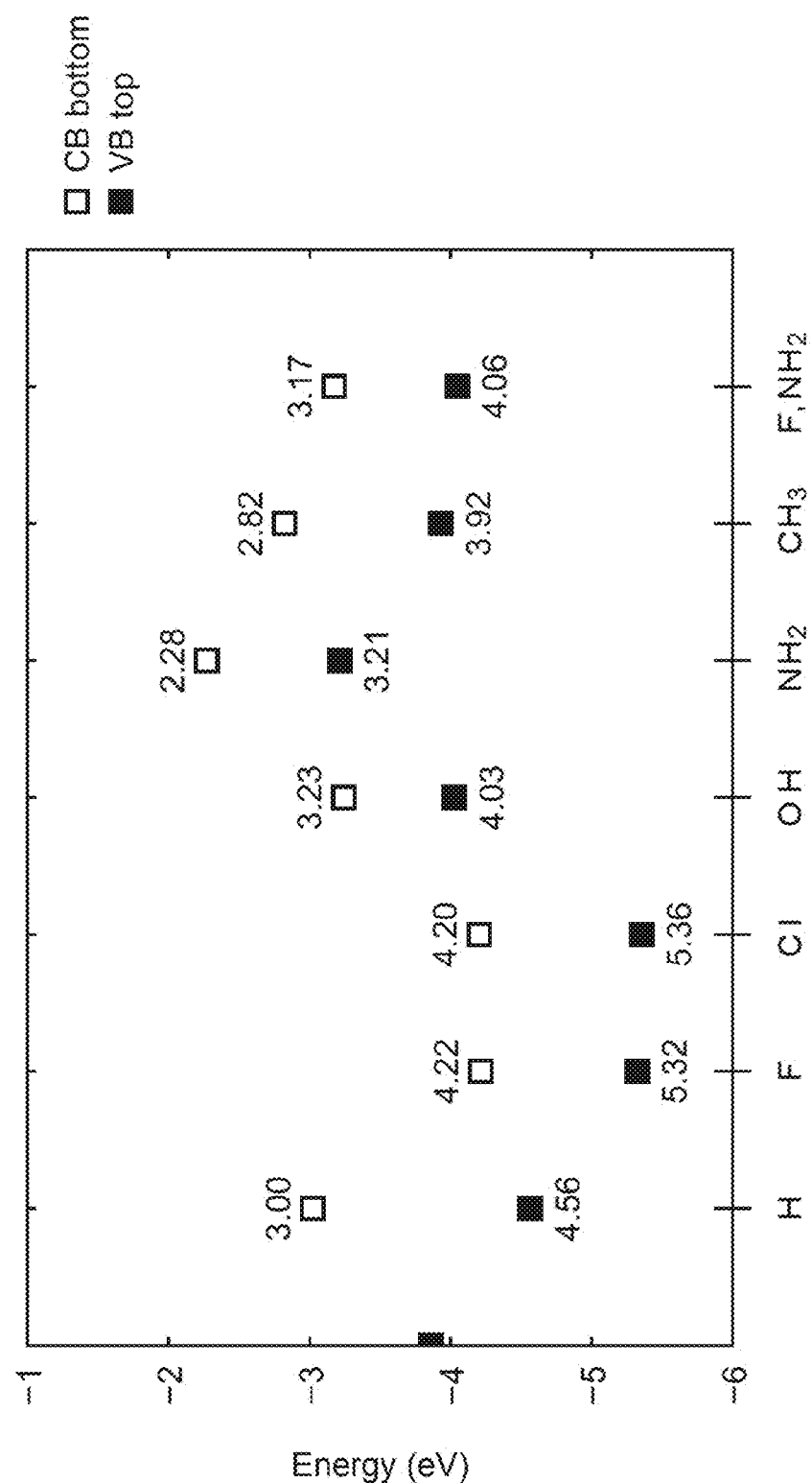
FIG. 3 is a chart representing energies at the bottoms of conduction bands and the tops of valence bands in the respective GNRs.

FIG. 2 illustrates band structures of GNRs when the modifying groups are variously changed. FIG. 3 represents energies at bottoms of conduction bands and tops of valence bands in the respective GNRs. Fermi levels of the respective GNRs are each located at the middle of the conduction band and the valence band. In FIG. 3, vacuum levels of the respective GNRs (Hartree Pot. of a vacuum region most distant from GNR) are made equal. FIG. 4 represents a table in which the energies at the bottoms of the conduction bands and the tops of the valence bands, the Fermi levels, and energy gaps in the respective GNRs are summarized. At this time, as the structure of each of the GNRs, an armchair GNR in which the number of dimer lines is seven as illustrated in FIG. 1 was assumed. It has been confirmed by the first-principles calculation that, when, for example, two kinds of such GNRs are combined to be bonded, a Fermi level of the resultant composite GNR has an about average value of Fermi levels of the respective GNRs.

Figure 5A:
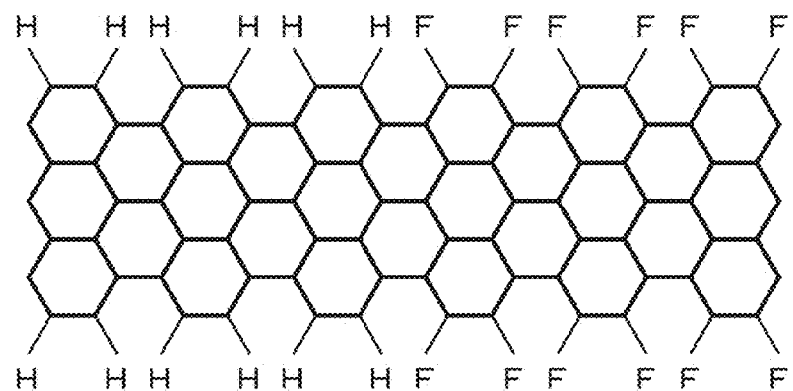
FIG. 5A and FIG. 5B are views illustrating a structure and an electron state of a composite GNR.
Figure 5B:
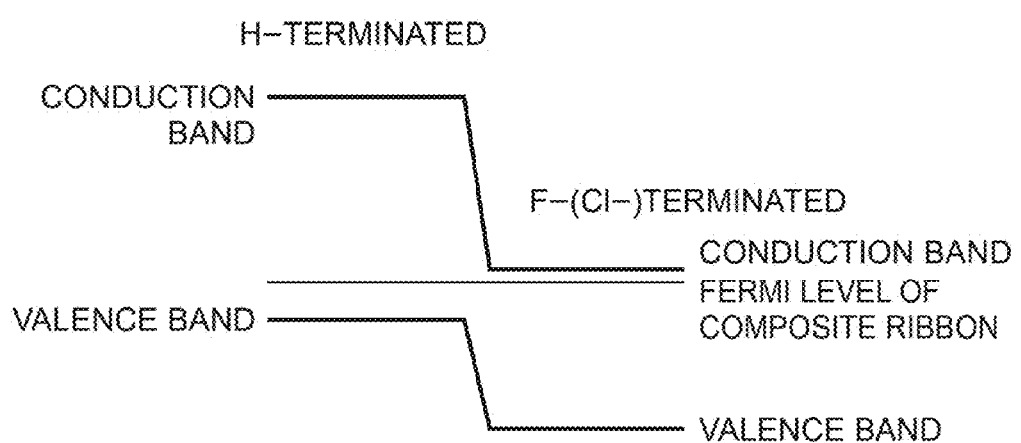

FIG. 5A illustrates a composite GNR which is a combination of GNRs terminated with hydrogen (H) and terminated with fluorine (F) (or terminated with chlorine (Cl)), and FIG. 5B illustrates an electron state (band alignment) of this composite GNR. In this case, one whose original Fermi level is shallower is p-doped and one whose original Fermi level is deeper is n-doped. That is, the H-terminated GNR is a p-type and the F-terminated GNR is an n-type, so that a pn junction is formed. Here, by using the Cl-terminated GNR instead of the F-terminated GNR, it is also possible to form substantially the same pn junction since the Fermi levels of the both are close to each other. Strictly speaking, the Fermi levels of the GNRs having the different modifying groups illustrated in FIG. 3 are all different, and therefore, by any combination of the GNRs presented in FIG. 3, the pn junction is formed. However, depending on a difference in the Fermi level and a difference in band gap, a doping degree differs, and generally, the larger the difference in the original Fermi level is, the stronger they are p- or n-doped. In the example presented in FIG. 3, when a F- or Cl-terminated GNR and a $NH_2$-terminated GNR are combined, the pn junction with the highest doping degree is formed.

Figure 6A:
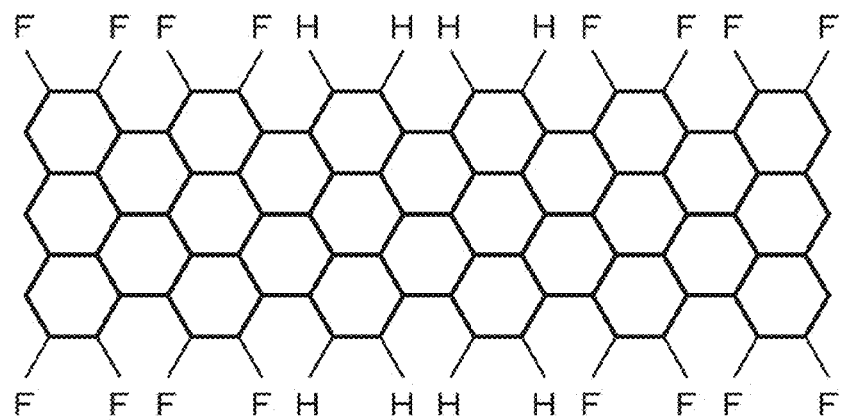
FIG. 6A and FIG. 6B are views illustrating a structure and an electron state of a composite GNR.
Figure 6B:
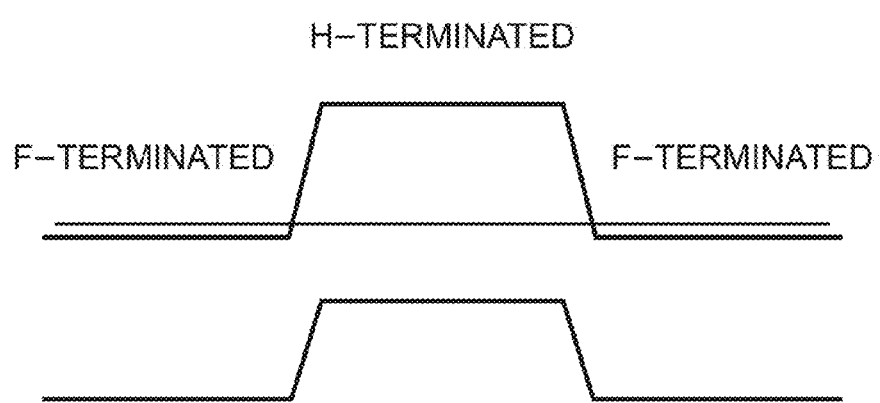

By combining the GNRs terminated with the different modifying groups as described above, it is possible to form not only a simple pn junction but also a pnp structure or an npn structure. FIG. 6A illustrates a composite GNR in which the npn structure is formed by combining F-terminated, H-terminated, and F-terminated GNRs, and FIG. 6B illustrates an electron state (band alignment) of this composite GNR. Conversely, by bonding H-terminated, F-terminated, and H-terminated GNRs, it is possible to form the pnp structure. It can be easily understood that such structures can be applied to a transistor. In this embodiment, the structure is used as a gas sensor by exposing only a center portion of the junction (the H-terminated portion in the npn structure in FIG. 6A, or the F-terminated portion in the pnp structure) to outside air.

Figure 7:
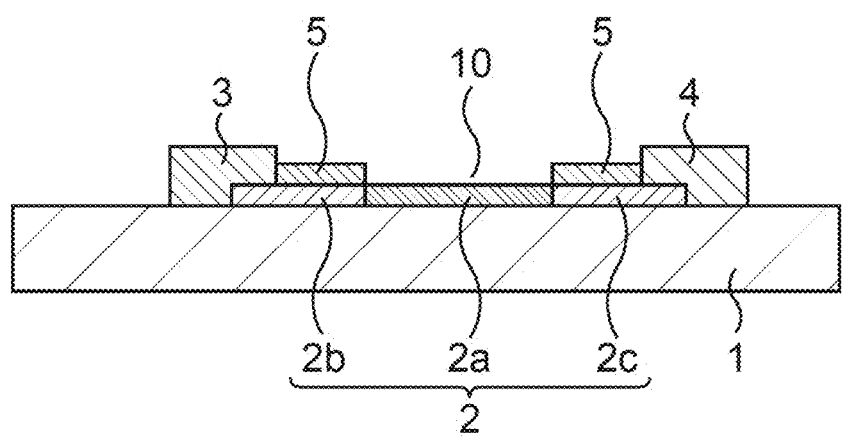
FIG. 7 is a schematic cross-sectional view illustrating an example of a gas sensor having an npn structure.

FIG. 7 is a schematic cross-sectional view illustrating an example of the gas sensor having the npn structure.

In this gas sensor, a channel layer 2 is formed on a silicon substrate 1 having an insulating film such as a silicon oxide film on a surface. The channel layer 2 has a 10 nm width or less in a short side direction and is formed by bonding a F-terminated GNR 2b to one end of a H-terminated GNR 2a and by bonding a F-terminated GNR 2c to the other end thereof. On an end portion of the F-terminated GNR 2b (an end portion on a side opposite to a connecting end to the H-terminated GNR 2a), for example, a source electrode 3 of Ti/Au is formed. On an end portion of the F-terminated GNR 2c (an end portion on a side opposite to a connecting end to the H-terminated GNR 2a), for example, a drain electrode 4 of Ti/Au is formed. On each of a surface of the F-terminated GNR 2b and a surface of the F-terminated GNR 2c, a protective film 5 made from a predetermined insulating material is formed. In this gas sensor, a surface of the H-terminated GNR 2a is exposed, and this exposed portion is a gas sensing part 10.

In the gas sensor of this embodiment, when the gas sensing part 10 being the exposed portion of the H-terminated GNR 2a is exposed to the outside air, a gas in the outside air is absorbed on the gas sensing part 10. Accordingly, a charge transfer or a modulation of the electron state occurs in the H-terminated GNR 2a, and its resistance value changes.

Figure 8:
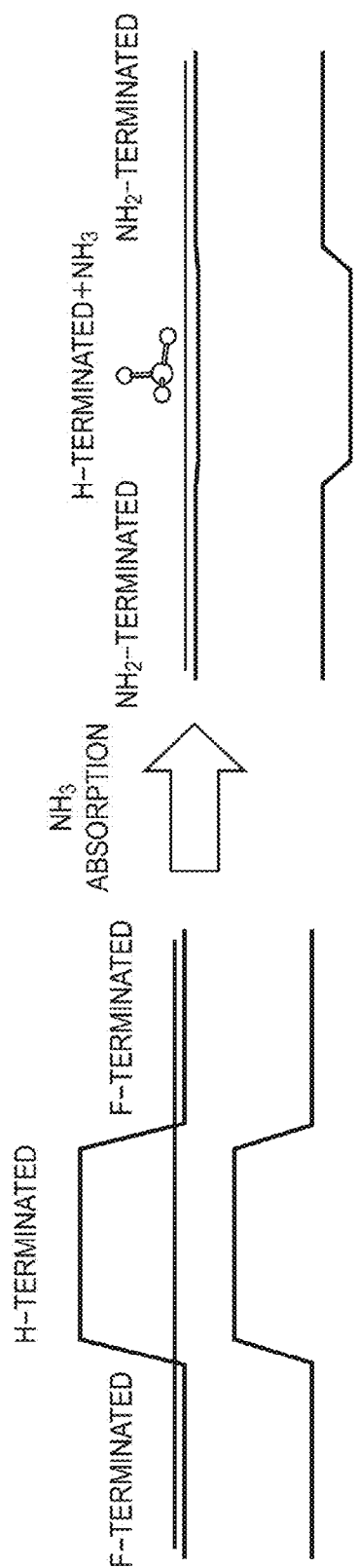
FIG. 8 is a schematic view illustrating an example of an electron state when a $NH_3$ gas is absorbed on a gas sensing part of the gas sensor and a charge transfer occurs in a H-terminated GNR.
Figure 9:
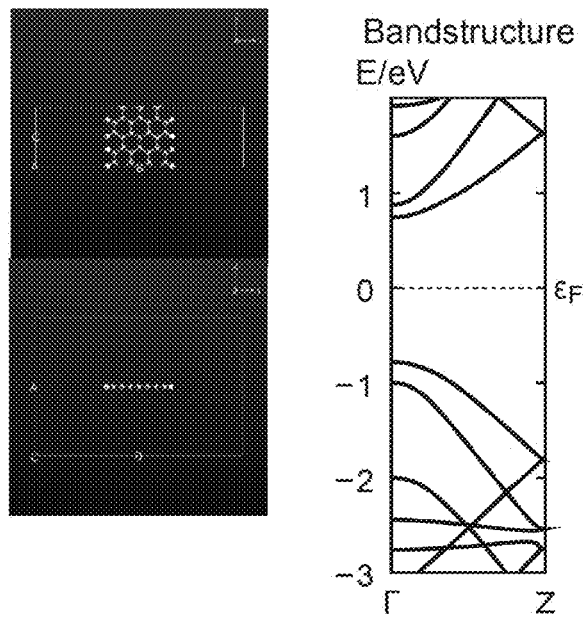
FIG. 9 is a schematic view illustrating a change of an electron state when $NH_3$ (+H) molecules adhere to the H-terminated GNR.
Figure 9:
Figure 9:
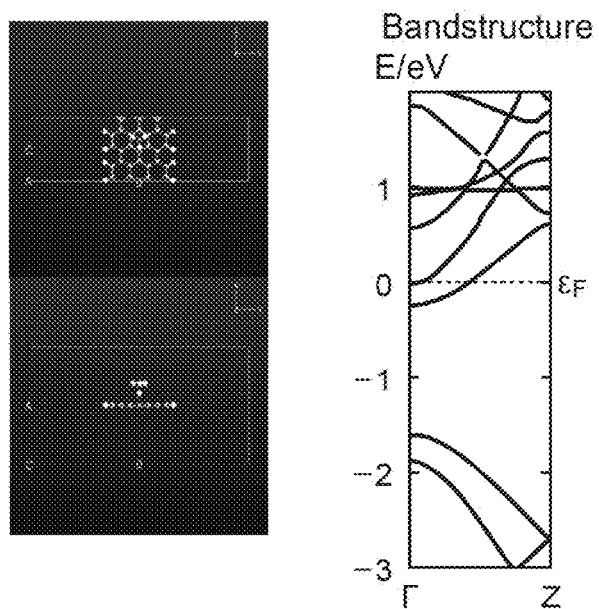

FIG. 8 is a schematic view illustrating an example of the electron state (band alignment) when a $NH_3$ gas is absorbed on the gas sensing part 10 of the gas sensor of this embodiment and the charge transfer occurs in the H-terminated GNR 2a. In this case, the electron state in the channel layer 2 largely changes from an off state to an on state. FIG. 9 is a schematic view illustrating the change of the electron state when $NH_3$ (+H) molecules adhere to the H-terminated GNR. As illustrated in FIG. 9, it is found that the GNR is largely electron-doped.

Figure 10:
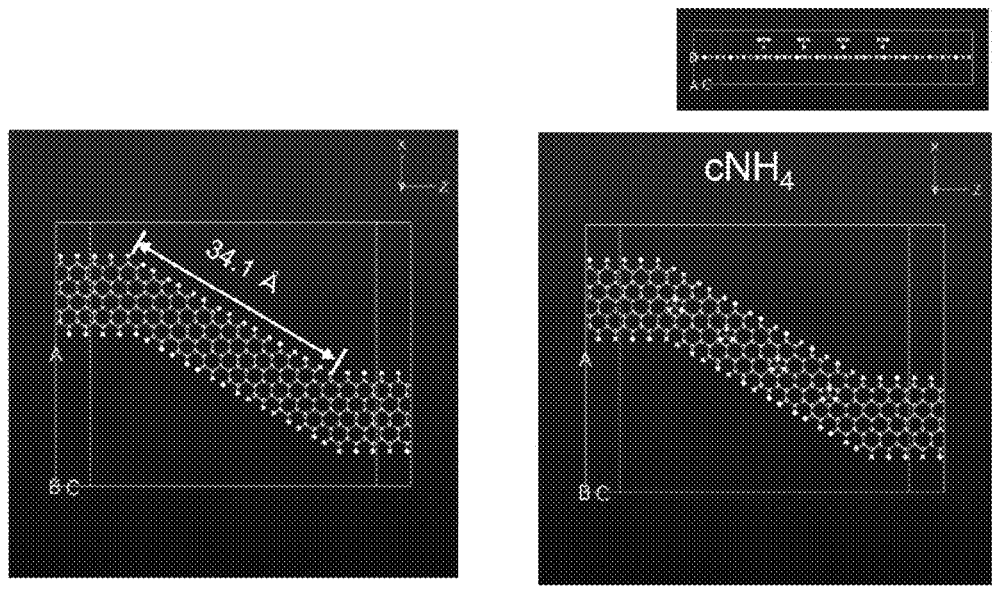
FIG. 10 is a schematic view illustrating a change of conductance when the $NH_3$ (+H) molecules adhere to the H-terminated GNR.
Figure 10:
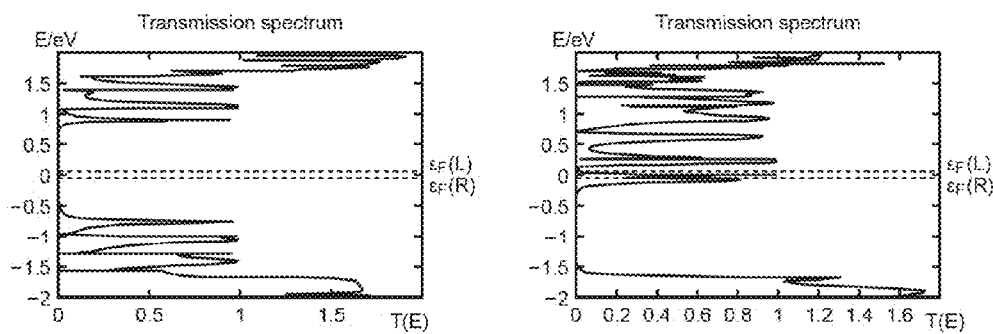

FIG. 10 is a schematic view illustrating a change of conductance when the $NH_3$ (+H) molecules adhere to the H-terminated GNR 2a. By the $NH_3$ (+H) molecules adhering to the H-terminated GNR 2a, compared with a state where the NH3 (+H) molecules do not adhere thereto, it is found that the conductance increases by about three orders of magnitude. Further, by combinations of the GNRs with the different modifying groups as illustrated in FIG. 2, it is possible to form various npn structures or pnp structures. Accordingly, it becomes possible to constitute gas sensors whose sensitivities are different for various kinds of gases.

Figure 11A:
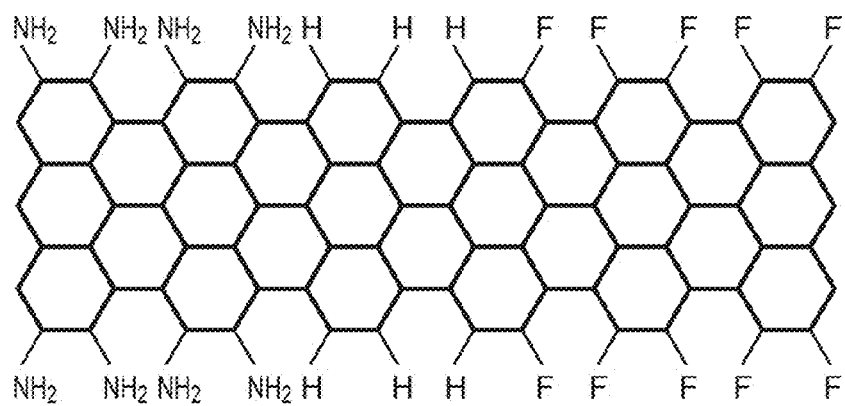
FIG. 11A and FIG. 11B are views illustrating a structure and an electron state of a composite GNR.
Figure 11B:
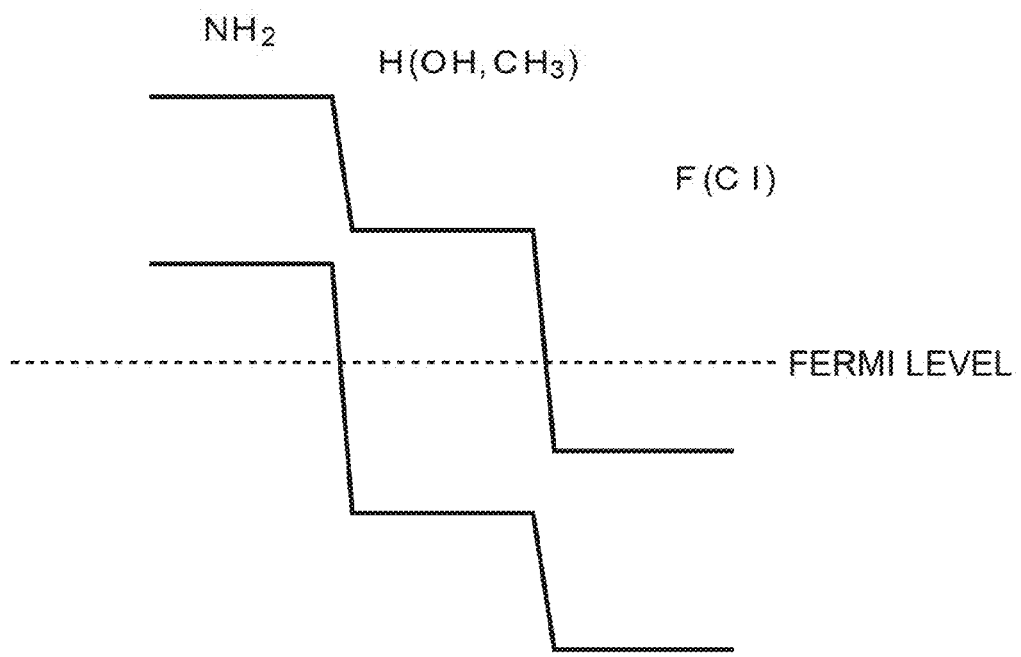

As the aforesaid combination of the GNRs terminated with the different modifying groups, it is possible to combine not only two kinds of GNRs but also three kinds of GNRs or more. This also makes possible to form more complicated doping structures of the GNRs. FIG. 11A illustrates a composite GNR formed by combining $NH_2$-terminated, H- (or OH- or $CH_3$-) terminated, and F- (or Cl-) terminated GNRs, and FIG. 11B illustrates an electron state (band alignment) of this composite GNR. In this case as well, Fermi level is substantially equal to an average of Fermi levels of the respective GNRs. As is seen from FIG. 7, it is possible to form a $p^+in^+$ structure which is a characteristic of a tunnel transistor. A part equivalent to i in such a structure is exposed to atmosphere, and is thereby used as a gas sensor.

Figure 12:
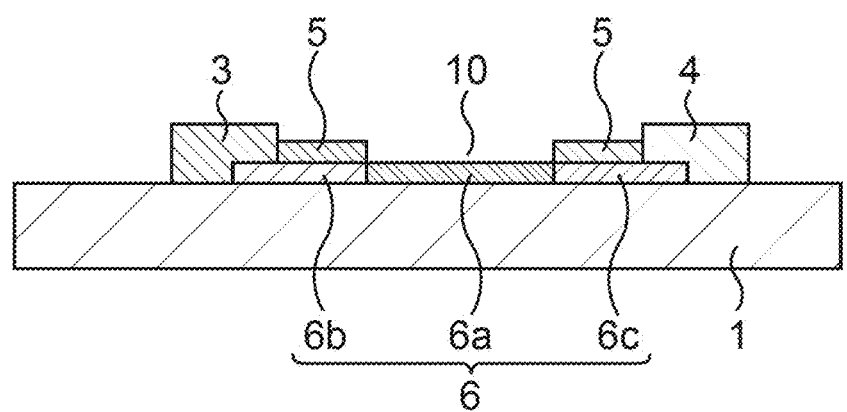
FIG. 12 is a schematic cross-sectional view illustrating an example of a gas sensor having a $p^+in^+$ structure.

FIG. 12 is a schematic cross-sectional view illustrating an example of the gas sensor having the $p^+in^+$ structure.

In this gas sensor, a channel layer 6 is formed on a silicon substrate 1 having an insulating film such as a silicon oxide film on a surface. The channel layer 6 has a 10 nm width or less in a short side direction and is formed by bonding a $NH_2$-terminated GNR 6b to one end of a H-terminated GNR 6a and by bonding a F-terminated GNR 6c to the other end thereof. On an end portion of the $NH_2$-terminated GNR 6b (an end portion on a side opposite to a connecting end to the H-terminated GNR 6a), for example, a source electrode 3 of Ti/Au is formed. On an end portion of the F-terminated GNR 6c (an end portion on a side opposite to a connecting end to the H-terminated GNR 6a), for example, a drain electrode 4 of Ti/Au is formed. On each of a surface of the $HN_2$-terminated GNR 6b and a surface of the F-terminated GNR 6c, a protective film 5 made from a predetermined insulating material is formed. In this gas sensor, a surface of the H-terminated GNR 6a is exposed, and this exposed portion is a gas sensing part 10.

As the source electrode 3 and the drain electrode 4, those whose work functions are close to a Fermi level of the channel layer 6 being a composite GNR are desirably used. According to calculation, the Fermi level of the channel layer 6 is about 3.8 eV. Therefore, in this case, it is necessary to select metal whose work function is relatively small, but in our calculation, there is a tendency for an absolute value of the Fermi level (measured from a vacuum level) to be smaller, and therefore, in this example, Ti is used as an electrode interface. Incidentally, in the example in FIG. 12, a $p^+$ side ($NH_2$-terminated GNR 6b side) is used as the source electrode, but an $n^+$ side (F-terminated GNR 6c side) may be used as the source electrode.

Figure 13A:
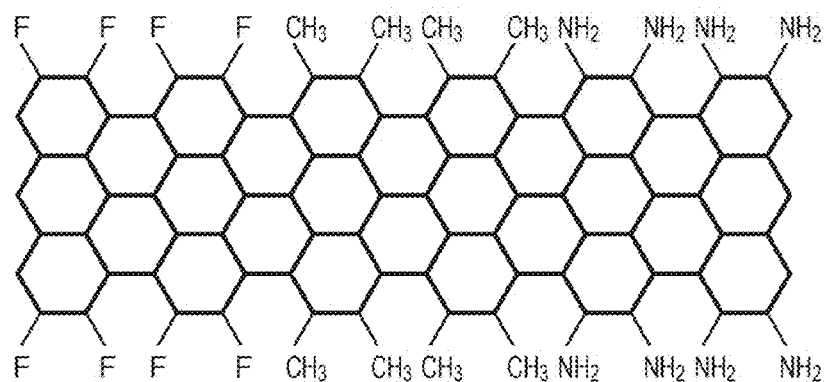
FIG. 13A and FIG. 13B are views illustrating a structure and an electron state of a composite GNR.
Figure 13B:
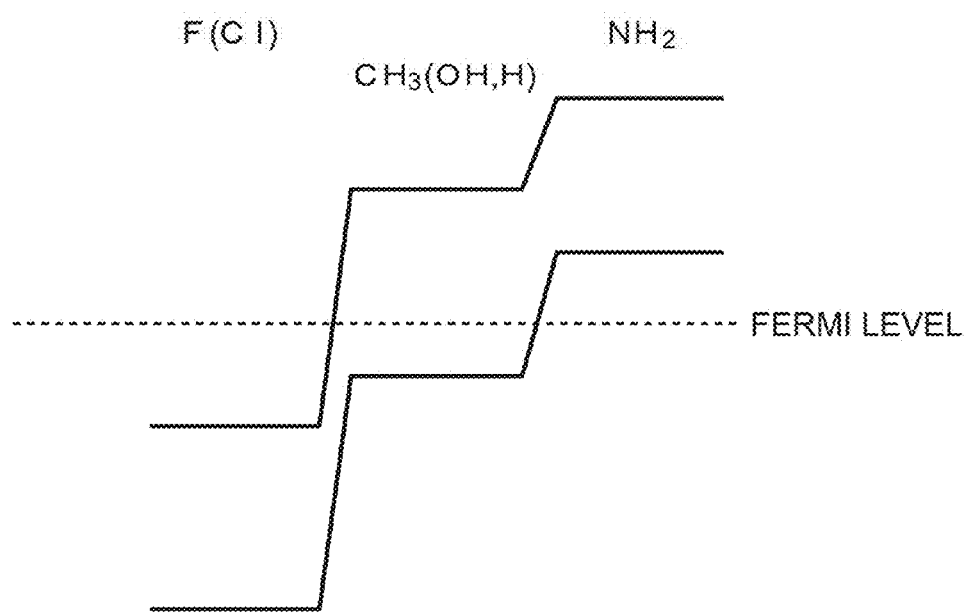

FIG. 13A illustrates a composite GNR combining F-terminated, $CH_3$- (or OH- or H-)terminated, and $NH_2$-terminated GNRs, and FIG. 13B illustrates an electron state (band alignment) of this composite GNR. In this case, an $n^+p^-p^+$ structure which is a characteristic of a tunnel transistor is formed, and a $p^-$ part is exposed to the atmosphere, and is thereby used as a gas sensor. In this case, it is also considered that, as a $p^+n^-n^+$ structure instead of the $n^+p^-p^+$ structure, an $n^-$ part is exposed to the atmosphere, and is thereby used as a gas sensor.

Figure 14:
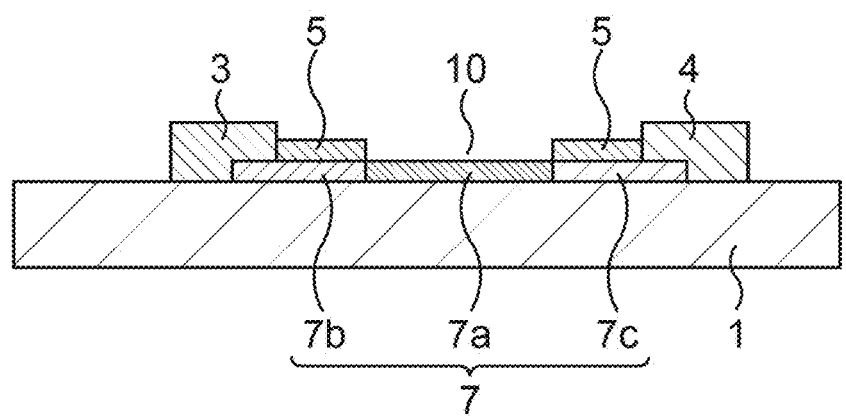
FIG. 14 is a schematic cross-sectional view illustrating an example of a gas sensor having an $n^+p^-\ p^+$ structure.

FIG. 14 is a schematic cross-sectional view illustrating an example of the gas sensor having the $n^+p^-p^+$ structure.

In this gas sensor, a channel layer 7 is formed on a silicon substrate 1 having an insulating film such as a silicon oxide film on a surface. The channel layer 7 has a 10 nm width or less in a short side direction and is formed by bonding a F-terminated GNR 7b to one end of a $CH_3$-terminated GNR 7a and by bonding a $NH_2$-terminated GNR 7c to the other end thereof. On an end portion of the F-terminated GNR 7b (an end portion on a side opposite to a connecting end to the $CH_3$-terminated GNR 7a), for example, a source electrode 3 of Ti/Au is formed. On an end portion of the $NH_2$-terminated GNR 7c (an end portion on a side opposite to a connecting end to the $CH_3$-terminated GNR 7a), for example, a drain electrode 4 of Ti/Au is formed. On each of a surface of the F-terminated GNR 7b and a surface of the $NH_2$-terminated GNR 7c, a protective film 5 made from a predetermined insulating material is formed. In this gas sensor, a surface of the $CH_3$-terminated GNR 7a is exposed, and this exposed portion is a gas sensing part 10.

As described above, by appropriately combining a plurality of GNRs having different terminating modifying groups to form the channel layers, it is possible to fabricate the gas sensors having various polarity combinations.

First Embodiment

Figure 15A:
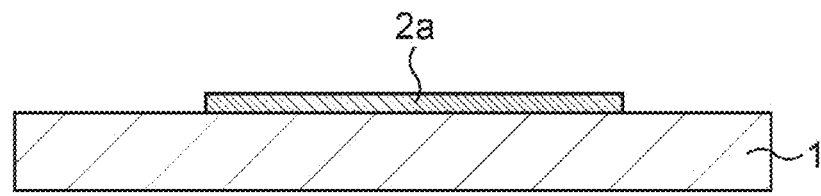
FIG. 15A to FIG. 15C are schematic cross-sectional views illustrating a method of manufacturing a gas sensor having a pnp structure according to a first embodiment in order of processes.
Figure 15B:
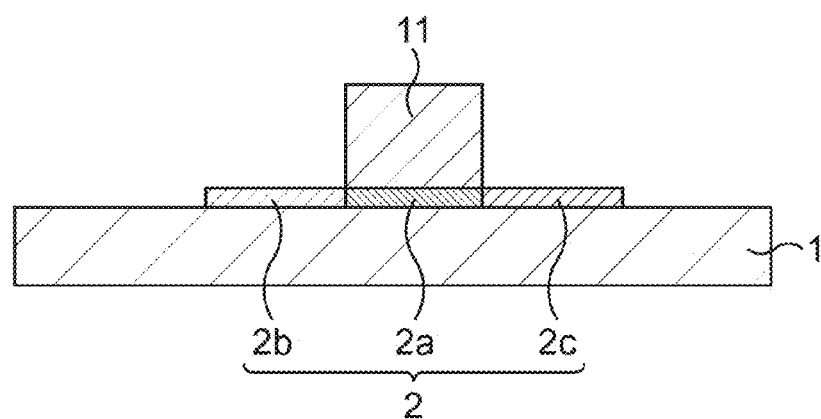
Figure 15C:
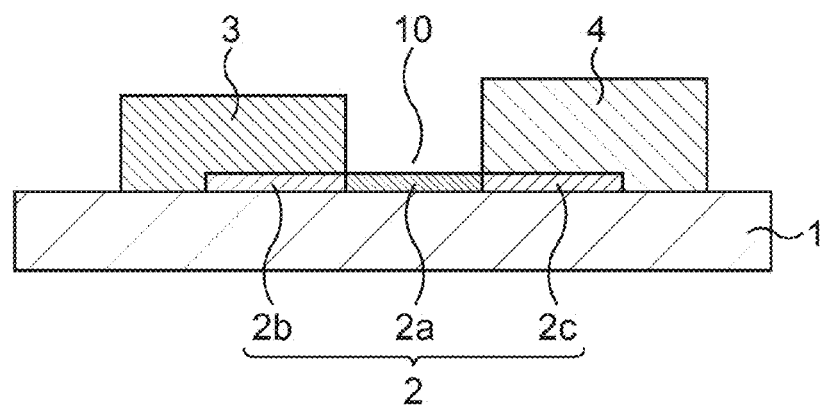

Hereinafter, a first embodiment will be described. In this embodiment, a gas sensor with an npn transistor structure using GNRs will be described together with its manufacturing method. FIG. 15A to FIG. 15C are schematic cross-sectional views illustrating the manufacturing method of the gas sensor having the npn structure according to the first embodiment in order of processes.

First, as illustrated in FIG. 15A, a H-terminated GNR 2a is formed.

In more detail, by using an anthracene dimer being a precursor of the GNR, whose edge portions are terminated with H, it is polymerized on a Au (111) substrate or on a Ag (111) substrate by heat energy. Note that the substrate is not limited to the one cited individually. Concretely, the same method as that of Non-Patent Document 1 is used. First, the anthracene dimer precursor is vapor-deposited on the Au (111) substrate or the Ag (111) substrate heated to, for example, about 180° C. to about 250° C. At this time, the anthracene dimer precursor is coupled on a straight line by radical polymerization.

Further, the substrate temperature is increased to, for example, about 350° C. to about 450° C. and this temperature is kept for about ten minutes to about twenty minutes. Consequently, due to a cyclodehydrogenation reaction, an armchair-type anthracene GNR which has a uniform width of about 0.7 nm and whose edge structure along a longitudinal direction is complete is formed.

Instead of the anthracene dimer, a pentacene dimer, a nonacene dimer, or the like can be also used. Consequently, the H-terminated GNR whose edge portions are H-terminated is formed.

Next, the H-terminated GNR is transferred onto a silicon substrate 1 having an insulating film such as a silicon oxide film on a surface. Consequently, the H-terminated GNR 2a is formed on the silicon substrate 1.

Subsequently, as illustrated in FIG. 15B, F-terminated GNRs 2b, 2c are formed in both end portions of the H-terminated GNR 2a.

In more detail, first, a resist is applied on the silicon substrate 1 so as to cover the H-terminated GNR 2a, and the resist is patterned by lithography. Consequently, a resist mask 11 from which the both end portions of the H-terminated GNR 2a are exposed is formed. Note that, instead of the resist mask 11, a sacrificial layer (metal or the like) capable of resisting a higher temperature may be formed, and may be used as the mask.

Next, the silicon substrate 1 is heated in a fluorine atmosphere, whereby the both exposed end portions of the H-terminated GNR 2a are fluorinated. Consequently, the F-terminated GNRs 2b, 2c are formed in the both end portions of the H-terminated GNR 2a. The resist mask 11 is removed by asking or wetting.

Subsequently, as illustrated in FIG. 15C, a source electrode 3 and a drain electrode 4 are formed.

In more detail, a resist is applied on the whole surface and the resist is patterned by lithography, but the mask used for the fluoridation in the above can be also used as it is. Consequently, a resist mask having openings from which the F-terminated GNRs or a part thereof is exposed is formed.

Next, metals (for example, Ti/Au) are deposited by a vapor deposition method or a sputtering method. Then, the resist mask and the Ti/Au deposited thereon are removed by lift-off. Consequently, the source electrode 3 and the drain electrode 4 are formed on the F-terminated GNR 2b and the F-terminated GNR 2c respectively. Here, a source electrode may be also formed on the F-terminated GNR 2c and a drain electrode may be also formed on the F-terminated GNR 2b.

Thus, the gas sensor with the npn structure according to this embodiment is formed. In this gas sensor, a surface of the H-terminated GNR 2a being a p part is exposed, and this exposed portion is a gas sensing part 10. This gas sensor can be utilized for sensing ammonia and the like as described above.

Incidentally, it is also possible to form a gas sensor having a pnp structure in the similar manner as that of this embodiment. In this case, for example, a center portion of a channel layer of GNR may be formed as a F-terminated GNR and its both end portions may be formed as H-terminated GNRs, and they may be bonded. Generally, with regard to an electron-donating gas molecule such as $NH_3$ it is preferred to use the gas sensor with the npn structure in which the p part is exposed, and with regard to an electron-accepting gas molecule such as NOX it is preferred to use the gas sensor with the pnp structure in which the n part is exposed, but the gas sensor of this embodiment is not necessarily limited thereto.

As described above, according to this embodiment, by using the channel layer 2 of the graphene whose polarity control is possible, the gas sensor with the npn structure having high reliability and high performance is fabricated.

Second Embodiment

Next, a second embodiment will be described. In this embodiment, a gas sensor with a $p^+in^+$ tunnel transistor structure using GNRs will be described together with its manufacturing method. FIG. 16A to FIG. 16D are schematic cross-sectional views illustrating the manufacturing method of the gas sensor having the $p^+in^+$ structure according to the second embodiment in order of processes.

Figure 16A:
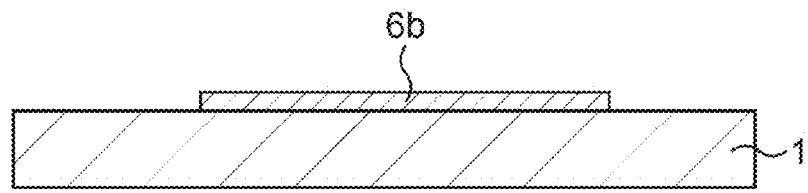
FIG. 16A to FIG. 16D are schematic cross-sectional views illustrating a method of manufacturing the gas sensor having the $p^+in^+$ structure according to a second embodiment in order of processes.

First, as illustrated in FIG. 16A, a $NH_2$-terminated GNR 6b is formed.

In more detail, by using an anthracene dimer being a precursor of the GNR, whose edge portions are terminated with $NH_2$, it is polymerized on a Au (111) substrate or a Ag (111) substrate by heat energy by the same method as that of the first embodiment. Instead of the anthracene dimer, a pentacene dimer, a nonacene dimer, or the like can be used. Consequently, the $NH_2$-terminated GNR whose edge portions are modified by $NH_2$ is formed.

Next, the $NH_2$-terminated GNR is transferred onto a silicon substrate 1 having an insulating film such as a silicon oxide film on a surface. Consequently, the $NH_2$-terminated GNR 6b is formed on the silicon substrate 1.

Figure 16B:
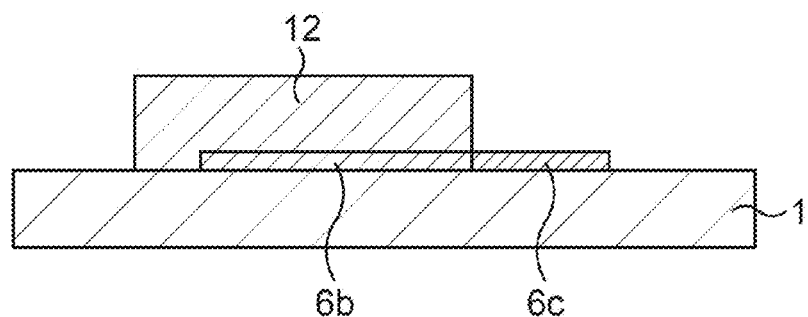

Subsequently, as illustrated in FIG. 16B, one-side portion of the $NH_2$-terminated GNRs 6b is formed into a F-terminated GNR 6c.

In more detail, first, a resist is applied on the silicon substrate 1 so as to cover the $NH_2$-terminated GNR 6b and the resist is patterned by lithography. Consequently, a resist mask 12 from which only the one-side (in the illustrated example, a right side) portion of the $NH_2$-terminated GNR 6b in FIG. 16A is exposed is formed. Note that, instead of the resist mask 12, a sacrificial layer (metal or the like) capable of resisting a higher temperature may be formed, and may be used as the mask.

Next, the silicon substrate 1 is heated in a fluorine atmosphere, whereby the right-side portion of the $NH_2$-terminated GNR 6b exposed from the resist mask 12 is fluorirated. Consequently, the F-terminated GNR 6c is formed in the right-side portion of the $NH_2$-terminated GNR 6b. The resist mask 12 is removed by asking or wetting.

Figure 16C:
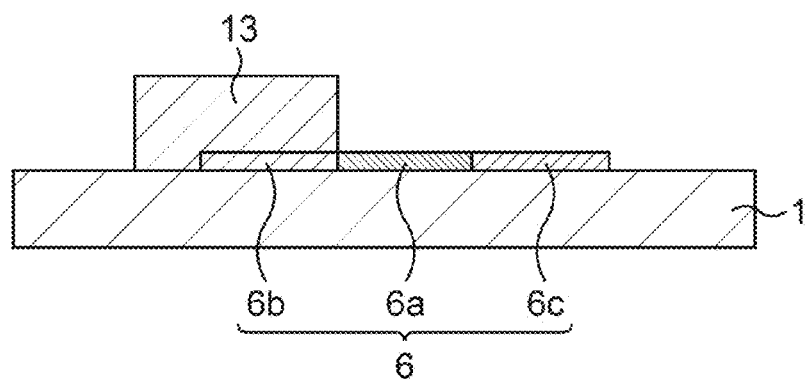

Subsequently, as illustrated in FIG. 16C, a center portion of the $NH_2$-terminated GNR 6b is formed into a H-terminated GNR 6a.

In more detail, first, the resist is applied on the silicon substrate 1 so as to cover the $NH_2$-terminated GNR 6b and the F-terminated GNR 6c, and the resist is patterned by lithography. Consequently, a resist mask 13 covering only the other side (in the illustrated example, a left side) portion of the $NH_2$-terminated GNR 6b and exposing the center portion of the $NH_2$-terminated GNR 6b and the F-terminated GNR 6c in FIG. 16B is formed. Note that, instead of the resist mask 13, the sacrificial layer (metal or the like) capable of resisting a higher temperature may be formed, and may be used as the mask.

Next, the silicon substrate 1 is heated in a hydrogen atmosphere. At this time, the structure of the F-terminated GNR 6c undergoes little change because the F-terminated GNR 6c is more stable to heat than a H-terminated GNR. On the other hand, the exposed portion of the $NH_2$-terminated GNR 6b becomes the H-terminated GNR 6a due to the heating. Consequently, a channel layer 6 in which the center portion is the H-terminated GNR 6a and the $NH_2$-terminated GNR 6b and the F-terminated GNR 6c are bonded to the left side and the right side of the H-terminated GNR 6a respectively is formed. The resist mask 13 is removed by asking or wetting.

Figure 16D:
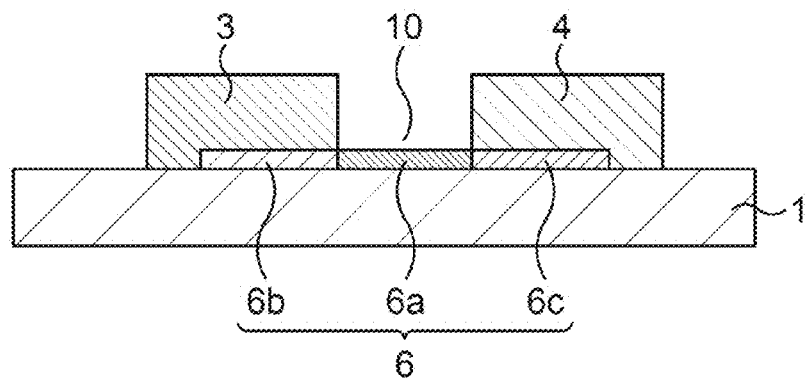

Subsequently, as illustrated in FIG. 16D, a source electrode 3 and a drain electrode 4 are formed.

In more detail, a resist is applied on the whole surface, and the resist is patterned by lithography. Consequently, a resist mask having openings from which the $NH_2$-terminated GNR 6b and the F-terminated GNR 6c are exposed is formed.

Next, metals (for example, Ti/Au) are deposited by a vapor deposition method or a sputtering method. Then, the resist mask and Ti/Au deposited thereon are removed by lift-off. Consequently, the source electrode 3 and the drain electrode 4 are formed on the $NH_2$-terminated GNR 6b and the F-terminated GNR 6c respectively. Here, a source electrode may be also formed on the F-terminated GNR 6c and a drain electrode may be also formed on the $NH_2$-terminated GNR 6b.

Thus, the gas sensor with the $p^+in^+$ structure is formed. In this gas sensor, a surface of the H-terminated GNR 6a being an i part is exposed, and this exposed portion is a gas sensing part 10. This gas sensor can be utilized for sensing NOX and the like.

As described above, according to this embodiment, by using the channel layer 6 of the graphene whose polarity control is possible, the gas sensor with the $p^+in^+$ structure having high reliability and high performance is fabricated.

Incidentally, it is also possible to form a gas sensor having an $n^+ip^+$ tunnel transistor structure in the similar manner as that of this embodiment. In this case, for example, a center portion of a channel layer of GNR may be formed as a H-terminated GNR, and its right side may be formed as a $NH_2$-terminated GNR, and its left side may be formed as a F-terminated GNR, and they may be bonded.

Third Embodiment

Figure 17:
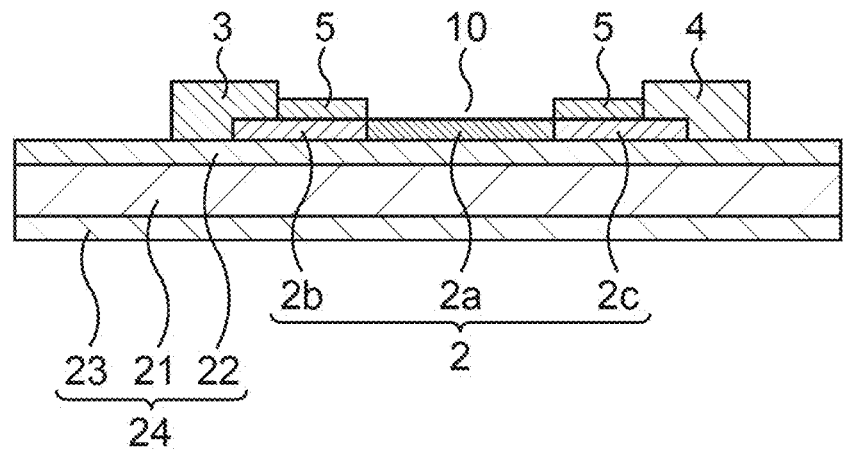
FIG. 17 is a schematic cross-sectional view illustrating an example of a gas sensor according to a third embodiment.

Next, a third embodiment will be described. In this embodiment, a structure in which a back gate is added to the gas sensor according to the first embodiment will be disclosed. FIG. 17 is a schematic cross-sectional view illustrating an example of a gas sensor according to this embodiment.

In this gas sensor, a channel layer 2 is formed above a silicon substrate 21 having a silicon oxide film 22 on a surface. A metal film 23 such as Ti/Au is formed on a rear surface of the silicon substrate 21. A back gate 24 is composed of the silicon substrate 21, the silicon oxide film 22, and the metal film 23 having low resistances. On the back gate 24, in the similar manner as that of the first embodiment, the channel layer 2 with an npn structure formed by bonding a F-terminated GNR 2b to one end of a H-terminated GNR 2a and by bonding a F-terminated GNR 2c to the other end thereof is formed. A source electrode 3 is formed on an end portion of the F-terminated GNR 2b and a drain electrode 4 is formed on an end portion of the F-terminated GNR 2c. Note that, in FIG. 17, the back gate is provided across the whole surface under the device but may be also provided under only the channel layer.

In this embodiment, the structure in which the back gate is added to the gas sensor with an npn structure is exemplified, but it is possible to apply to a gas sensor provided with GNRs terminated with a plurality of different modifying groups such as a $p^+in^+$ structure and an $n^+p^-p^+$ structure as a channel layer.

In this embodiment, by using the channel layer 2 of the graphene whose polarity control is possible, the gas sensor with the npn structure having high reliability and high performance is fabricated. Further, by providing the back gate 24, it is possible to control a threshold for a response of the gas sensor as well as to change a threshold when a top-gate is placed in a transistor.

Forth Embodiment

Figure 18:
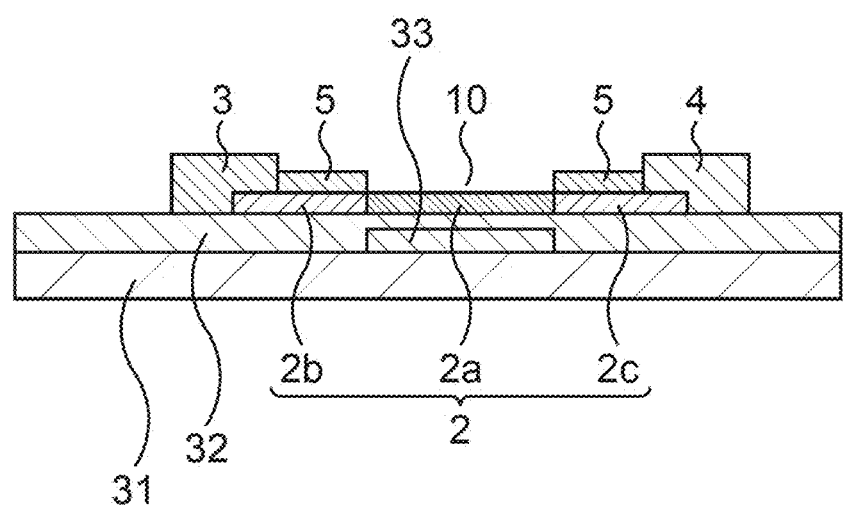
FIG. 18 is a schematic cross-sectional view illustrating an example of a gas sensor according to a forth embodiment.

Next, a forth embodiment will be described. In this embodiment, a structure in which a heater layer is added to the gas sensor according to the first embodiment will be disclosed. FIG. 18 is a schematic cross-sectional view illustrating an example of a gas sensor according to this embodiment.

In this gas sensor, for example, a heater layer 33 is arranged in a silicon oxide film 32 on a silicon substrate 31. The heater layer 33 is, what is called, a resistor, and can be formed by using metal, a semiconductor, graphene, carbon nanotube, and the like. On a portion corresponding to above the heater layer 33, a channel layer 2 with an npn structure formed by bonding a F-terminated GNR 2b to one end of a H-terminated GNR 2a and by bonding a F-terminated GNR 2c to the other end thereof is formed. A source electrode 3 is formed on an end portion of the F-terminated GNR 2b and a drain electrode 4 is formed on an end portion of the F-terminated GNR 2c. In this embodiment, for example, after use of the gas sensor, the heater layer 33 generates heat by conducting electricity to the heater layer 33, so that the channel layer 2 is locally heated. Accordingly, gas molecules absorbed on a gas sensing part 10 can be securely desorbed therefrom.

In this embodiment, the structure in which the heater is added to the gas sensor with an npn structure is exemplified, but it is possible to apply to a gas sensor provided with GNRs terminated with a plurality of different modifying groups such as a $p^+in^+$ structure and an $n^+p^-p^+$ structure as a channel layer.

In this embodiment, by using the channel layer 2 of the graphene whose polarity control is possible, the gas sensor with the npn structure having high reliability and high performance is fabricated. Further, by providing the heater layer 33, it is possible to desorb the absorbed gas molecules and to make the gas sensor a reset state.

Note that, regarding the npn structure and the pnp structure in the above-described channel layer with a composite GNR, various junctions are formed by combinations of GNRs whose Fermi levels are different. FIG. 19A and FIG. 19B represent an example of the combinations, and FIG. 19A represents concrete examples of the npn structure and FIG. 19B represents concrete examples of the pnp structure. Here, for example, F—OH—F represents the composite GNR in which a F-terminated GNR is bonded to one end and the other end of a OH-terminated GNR, and a numerical value in parentheses represents the Fermi level.

According to the embodiments, a gas sensor in which a channel layer of graphene whose polarity control is possible is used and highly-sensitive and highly-selective gas sensing can be performed is fabricated.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A gas sensor comprising:
    a channel layer formed of a plurality of graphene bonded to each other, among which adjacent graphene have edge portions terminated with modifying groups different from each other; and
    a pair of electrodes formed on both ends of the channel layer, wherein
    in the channel layer, a part of a surface thereof is exposed, and the exposed portion is a gas sensing part.

2. The gas sensor according to claim 1, wherein the adjacent graphene have different Fermi levels in a state before being bonded to each other.

3. The gas sensor according to claim 1, wherein the modifying groups are two kinds or three kinds or more selected from H, F, Cl, OH, $NH_2$, and $CH_3$.

4. The gas sensor according to claim 1, wherein, in two kinds of the graphene bonded to each other, one is n-doped and the other is p-doped.

5. The gas sensor according to claim 1, wherein the channel layer constitutes a pnp structure or an npn structure by the graphene being bonded to each other.

6. The gas sensor according to claim 1, wherein the channel layer constitutes a $p^+n^-$ (or i)$n^+$ structure or an $n^+p^-$(or i)$p^+$ structure by the graphene being bonded to each other.

7. The gas sensor according to claim 1, wherein the channel layer has a 10 nm width or less in a short-side direction thereof.

8. The gas sensor according to claim 1, comprising a back gate structure under the channel layer.

9. The gas sensor according to claim 1, comprising a heater layer below the channel layer.

10. A method of manufacturing a gas sensor comprising:
    forming a piece of graphene whose edge portion is terminated with one modifying group;
    forming at least part of the piece of graphene into another piece of graphene whose edge portion is terminated with another modifying group different from the one modifying group to form a channel layer in which the piece of graphene and the other piece of graphene are bonded to each other; and forming a pair of electrodes on both ends of the channel layer, wherein a part of a surface of the channel layer is exposed, and the exposed portion is a gas sensing part.

11. The method of manufacturing the gas sensor according to claim 10, wherein the other piece of graphene is two kinds or three kinds or more of graphene whose edge portions are terminated with modifying groups different from each other.

12. The method of manufacturing the gas sensor according to claim 10, wherein the piece of graphene and the other piece of graphene have different Fermi levels in a state before being bonded to each other.

13. The method of manufacturing the gas sensor according to claim 10, wherein the modifying groups are two kinds or three kinds or more selected from H, F, Cl, OH, $NH_2$, and $CH_3$.

14. The method of manufacturing the gas sensor according to claim 10, wherein the channel layer has a 10 nm width or less in a short-side direction thereof.

15. The method of manufacturing the gas sensor according to claim 10, wherein in the piece of graphene and the other piece of graphene bonded to each other, one is n-doped and the other is p-doped.

16. The method of manufacturing the gas sensor according to claim 10, wherein the channel layer constitutes a pnp structure or an npn structure by the piece of graphene and the other piece of graphene being bonded to each other.

17. The method of manufacturing the gas sensor according to claim 10, wherein the channel layer constitutes a $p^+n^-$(or i)$n^+$ structure or an $n^+p^-$(or i)$p^+$ structure by the piece of graphene and the other piece of graphene being bonded to each other.

* * * * *